United States Patent
Heppell

(10) Patent No.: US 10,701,043 B2
(45) Date of Patent: Jun. 30, 2020

(54) METHODS FOR PHYSICAL AUTHENTICATION OF MEDICAL DEVICES DURING WIRELESS PAIRING

(71) Applicant: TC1 LLC, St. Paul, MN (US)

(72) Inventor: Kevin Heppell, Portland, OR (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/229,807

(22) Filed: Dec. 21, 2018

(65) Prior Publication Data
US 2019/0222564 A1 Jul. 18, 2019

Related U.S. Application Data

(60) Provisional application No. 62/618,464, filed on Jan. 17, 2018.

(51) Int. Cl.
| | | |
|---|---|---|
| *H04L 29/06* | (2006.01) | |
| *G16H 40/40* | (2018.01) | |
| *H04W 12/04* | (2009.01) | |
| *A61M 1/12* | (2006.01) | |
| *H04W 12/06* | (2009.01) | |

(52) U.S. Cl.
CPC ......... *H04L 63/0435* (2013.01); *A61M 1/122* (2014.02); *G16H 40/40* (2018.01); *H04L 63/061* (2013.01); *H04W 12/04* (2013.01); *H04W 12/06* (2013.01); *H04L 63/0492* (2013.01); *H04L 63/18* (2013.01)

(58) Field of Classification Search
CPC ..... A61M 1/122; H04W 12/06; H04L 63/061; H04L 63/0492; H04L 63/0435; G16H 40/20
See application file for complete search history.

(56) References Cited

U.S. PATENT DOCUMENTS

| | | |
|---|---|---|
| 5,695,471 A | 12/1997 | Wampler |
| 6,071,093 A | 6/2000 | Hart |
| 6,116,862 A | 9/2000 | Rau et al. |
| 6,186,665 B1 | 2/2001 | Maher et al. |
| 6,234,772 B1 | 5/2001 | Wampler et al. |
| 6,264,635 B1 | 7/2001 | Wampler et al. |
| 6,888,861 B2 | 5/2005 | Taguchi et al. |
| 7,699,586 B2 | 4/2010 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,652,024 B1 | 2/2014 | Yanai et al. |
| 8,668,473 B2 | 3/2014 | LaRose et al. |

(Continued)

*Primary Examiner* — Hongmin Fan
(74) *Attorney, Agent, or Firm* — Kilpatrick Townsend & Stockton LLP

(57) ABSTRACT

Systems and methods for physical authentication of medical devices during wireless pairing are disclosed herein. The method can include receiving a request to initiate coupling. Following the request, a visual identifier can be generated with a light source. The visual identifier can include embedded data used to couple the medical devices. The visual identifier can be captured in image data, which image data can be analyzed and the embedded data can be extracted from the image data. Based on the embedded data that is extracted from the image data, secure coupling between medical devices can be established.

21 Claims, 6 Drawing Sheets

(56) References Cited

U.S. PATENT DOCUMENTS

| | | |
|---|---|---|
| 2007/0078293 A1 | 4/2007 | Shambaugh et al. |
| 2008/0021394 A1 | 1/2008 | LaRose et al. |
| 2009/0067846 A1* | 3/2009 | Yu .................... H04B 10/1143 398/128 |
| 2009/0203957 A1 | 8/2009 | LaRose et al. |
| 2012/0046514 A1 | 2/2012 | Bourque |
| 2012/0095281 A1 | 4/2012 | Reichenbach et al. |
| 2013/0096364 A1 | 4/2013 | Reichenbach et al. |
| 2013/0121821 A1 | 5/2013 | Ozaki et al. |
| 2013/0170970 A1 | 7/2013 | Ozaki et al. |
| 2013/0225909 A1 | 8/2013 | Dormanen et al. |
| 2015/0076989 A1* | 3/2015 | Walma .................. H04B 10/40 315/149 |
| 2017/0325091 A1* | 11/2017 | Freeman ............... H04W 12/06 |
| 2018/0063681 A1* | 3/2018 | Mankovskii ........... H04W 4/33 |

\* cited by examiner

METHODS FOR PHYSICAL AUTHENTICATION OF MEDICAL DEVICES DURING WIRELESS PAIRING

CROSS REFERENCE TO RELATED APPLICATIONS

The present application claims the benefit of U.S. Provisional Patent Application No. 62/618,464 filed Jan. 17, 2018, entitled "METHODS FOR PHYSICAL AUTHENTICATION OF MEDICAL DEVICES DURING WIRELESS PAIRING; the entirety of which is hereby incorporated herein by reference for all purposes.

BACKGROUND

This application relates generally to secure coupling of medical devices and more specifically relates to secure coupling of components in mechanical circulatory support systems.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

As VAD systems continue to develop and are more widely used, the importance of reliability continues to increase. One area for potential improvement can be found in the establishment of initial communication (pairing) between two wireless devices. In instances when a secure connection is desired, a set of security keys or other unique identifiers can be required. However, use of such security keys can require human interaction with the devices, or can require the transmission of the keys between devices. Alternatively, some devices include a display that is used to provide a text string corresponding to a security key. This can be read by a human operator and can be entered into another device. However, this can be impractical as it requires human intervention and allows for the possibility of human error in entering the security key. Thus, new methods, systems, and devices that will improve coupling of the VAD systems and/or of other devices are desired.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Aspects of the present disclosure relate to systems and methods for securely coupling two medical devices. These methods can include the generating of a visual indicator with a first device that can be either visible or non-visible to the human eye. A second device can capture image data which can be evaluated to determine the presence or absence of the visual indicator. If the visual indicator is identified in the image data, then a secure connection can be established between the first and second devices. In some embodiments, a security key can be transmitted between the first and second devices via the manipulation of the visual indicator, or alternatively, information in addition to the security key can be transmitted between the devices via the manipulation of the visual indicator.

One aspect of the present disclosure relates to a method of bi-modal communication between medical devices. The method includes: generating a visual identifier of a first medical device by the first medical device; directing capture of image data of an unidentified medical device with a second medical device; determining that the unidentified medical device is the first medical device based on the captured image data; and establishing a secure communication connection between the first and second medical devices.

In some embodiments, the image data can include any image data including, for example, a series of time-sequential images, and in some embodiments, for example, the image data can include video data. In some embodiments, determining that the unidentified medical device is the first medical device includes identifying the visual identifier within the image data. In some embodiments, generating the visual identifier can include modulation of a light source of the first medical device. In some embodiments, modulation of the light source of the first medical device can include modulating at least one of: an intensity of the light source of the first medical device; a frequency of the light source; or a frequency of light emitted by the light source.

In some embodiments, identifying the visual identifier within the image data can include identifying the modulation of the light source of the first medical device and extracting data from the identified modulation of the light source of the first medical device. In some embodiments, determining that the unidentified medical device is the first medical device based on the captured image data can include comparing the modulation of the light source as captured in the image data to the modulation of the light source. In some embodiments, determining that the unidentified medical device is the first medical device can include identifying a shape of the first medical device within the image data.

In some embodiments, the method can include transmitting data from the first medical device to the second medical device via modulation of a light source subsequent to establishing a secure communication connection between the first and second medical devices. In some embodiments, the method can include: capturing follow-on image data of the modulation of the light source subsequent to establishing a secure communication connection between the first and second medical devices; and extracting transmitted data from the follow-on image data.

In some embodiments, the method can include transmitting data from the second medical device to the first medical device. In some embodiments, data is transmitted from the second medical device to the first medical device via a wireless communication. In some embodiments, the data is transmitted from the second medical device to the first medical device in response to the captured image data.

One aspect of the present disclosure relates to a system including a first medical device and a second medical device. The first medical device can include: an antenna; a visual output; and a processor. In some embodiments, the processor can operate according to stored instructions to generate a first visual identifier comprising data identifying the first medical device with the visual output. The second medical device can include: an antenna; a camera that can capture image data; and a processor. In some embodiments, the processor can operate according to stored instructions to: identify the visual identifier within the captured image data; extract data from the visual identifier as captured in the image data; and establish a secure communication connection with the first medical device based on the data extracted from the visual identifier as captured in the image data.

In some embodiments, the captured image data can include a series of time-sequential images. In some embodiments, generating the visual identifier can include directing modulation of a light source of the first medical device. In some embodiments, identifying the visual identifier within the image data can include identifying the modulation of the light source of the first medical device and extracting data from the identified modulation of the light source of the first medical device. In some embodiments, the processor of the first medical device can transmit data from the first medical device to the second medical device via modulation of a light source subsequent to establishing a secure communication connection between the first and second medical devices.

In some embodiments, the camera can capture follow-on image data of the modulation of the light source subsequent to establishing a secure communication connection between the first and second medical devices. In some embodiments, the processor of the second medical device can extract transmitted data from the follow-on image data. In some embodiments, the second medical device can include an antenna. In some embodiments, the first and second medical devices can wirelessly communicate via the antenna of the first medical device and the antenna of the second medical device.

For a fuller understanding of the nature and advantages of the present invention, reference should be made to the ensuing detailed description and accompanying drawings.

DETAILED DESCRIPTION

Figure 1:
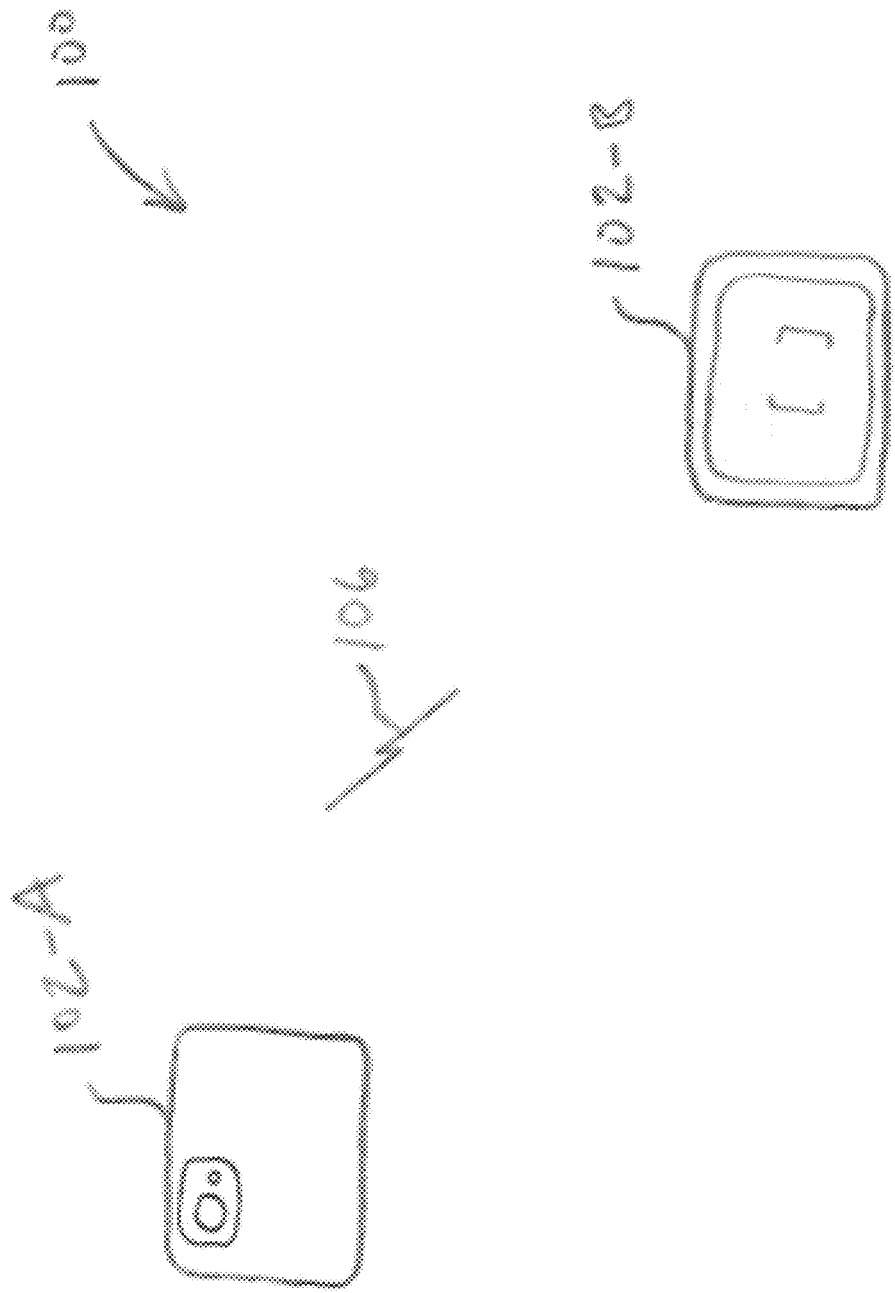
FIG. 1 is a perspective view of one embodiment of a medical device network.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Increasingly, devices including medical devices such as VADs interact with each other as nodes within a network of devices. This interconnection between devices allows rapid transfer of large amounts of information gathered by the devices and can allow the coordination of multiple devices to achieve a desired effect. While such interaction and communication between devices can be greatly beneficial, and in the case of medical devices, can allow treatment of previously difficult conditions or allow wholistic treatment of a body as opposed to treatment at a single location, these communications and interactions increase the security risks to individual devices as well as to groups of devices. Further, as the number of devices increases, the number of potential vulnerable access points to a device or to a network of devices increases.

To minimize these risks, coupling techniques have been developed that provide some level of security, in many instances via the use of one or several security keys. However the use of these security keys is not without problems that can limit the ability to couple or the security of the coupling of devices. In some embodiments, for example, these security keys can be communicated between devices by human intervention, and specifically by a human reading the security key from a display of a first device and then entering this key into a second device. Based on this security key, the second device can securely couple with the first device. While this human intervention can improve some aspects of security, it can also be error-prone, time consuming, and tedious.

Some embodiments of the present disclosure improve communication between devices via coupling or communication based on a combination of a visual output and image data. This can include the transmission of a security key via manipulation of a visual output and analysis of gathered image data, which security key can be used to couple devices and to establish a secure, radio wave-based wireless connection, via which radio wave-based wireless connection further data can be transmitted. In some embodiments, data other than a security key can be transmitted via manipulation of a visual output and gathering and analysis of image data.

Further, these methods and systems create bi-modal communication possibilities wherein the security key can be automatically transmitted from one device to another device via a communication channel that is not easily interfered with or intercepted. Further, because of the direct exchange of this security key, the risk of human error is minimized.

Referring now to the drawings, in which like reference numerals represent like parts throughout the several views, FIG. 1 shows a perspective view of one embodiment of a medical device network 100. The medical device network 100 can comprise at least two devices 102 that can be, for example, medical devices and/or controllers. As specifically depicted in FIG. 1, the medical device network 100 can include a first device 102-A, which can be a first medical device, and a second device 102-B, which can be a second medical device. The first and second devices 102-A, 102-B can be any desired type of medical devices including, for example, non-implantable medical devices and/or implantable medical devices such as, for example, active implantable medical devices, passive implantable medical devices, a pacemaker, a blood pump, a ventricle assist device (VAD), a neurostimulator, a sensor, an implantable cadioverter defibrillator, a cochlear implant, an implantable infusion pump, an implantable glucose monitor, or the like. In some embodiments, the non-implantable medical devices can include, for example, an external charger, an external controller, an external blood pump, an external pacemaker, a sensor, an external neurostimulator, or the like. The first and second devices 102-A, 102-B can each be the same type of medical device or can be different types of medical devices. In one embodiment, for example, the first device 102-A can comprise an implantable blood pump and the second device 102-B can comprise an external controller that can communicate with the implantable blood pump to control the operation or aspects of the operation of the implantable blood pump. Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

In some embodiments, the medical devices 102-A, 102-B can be communicatingly coupled. In some embodiments, this coupling can be via wireless communications 106. These wireless communications 106 can be via radio wave and/or via a visual identifier. In some embodiments, this coupling can be a hybrid coupling, also referred to herein as a bi-modal coupling that includes some communications transmitted via radio wave and some communications transmitted via the visual identifier.

Figure 2:
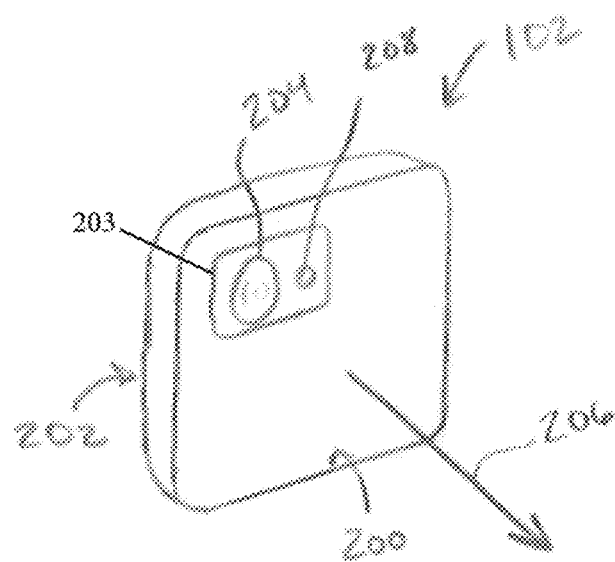
FIG. 2 is a front view of one embodiment of a medical device.

A front view of one embodiment of a device 102 is shown in FIG. 2. The device 102 can comprise a variety of shapes and sizes. In some embodiments, the medical device can include a front 200 and a back 202. The front 200 of the device 102 can include, a pairing module 203 that can generate electromagnetic radiation (EMR) and can detect EMR generated by another device 102. In some embodiments, the pairing module 203 can be used to pair multiple two or more devices via generation and/or detection of EMR encoded with data identifying one or more of the two or more devices. The pairing module 203 can include a visual output 204, also referred to herein as a light source 204. The visual identifier can generate EMR which can be in the form of, for example, visible or non-visible radiation. The visual output 204 can comprise, for example, a Light Emitting Diode (LED), a laser, a laser diode, or the like.

The light source 204 can generate EMR traveling in one or several directions from the light source 204. In some embodiments, the EMR can travel in all directions away from the light source 204 and from the device 102, and in some embodiments, the EMR can travel in a limited number of directions. In the embodiment depicted in FIG. 2, the light source 204 can deliver EMR in a forward-direction as indicated by arrow 206.

The device 102, and specifically the pairing module 203, can further comprise an image data generator 208. The image data generator 208 can comprise a variety of shapes and size and can be located in any desired location on the device 102. In some embodiments, the image data generator 208 can comprise a camera, a photo sensor, or the like. While the embodiment of FIG. 2 depicts the device 102 including both the visual output 204 and the image data generator 208, the device 102 can include only the visual output 204, on the image data generator 208, or both the visual output 204 and the image data generator 208.

In some embodiments, the image data generator 208 can be directional and can detect EMR and/or generate image data in one direction. In some embodiments in which the device 102 includes both the visual output 204 and the image data generator 208, the visual output 204 and the image data generator 208 can have the same orientation and/or can have different orientations. In some embodiments, and as depicted in FIG. 2, the visual output 204 can generate EMR in the direction indicated by arrow 206 and image data generator 208 can have the same orientation to allow generation of image data from EMR traveling in the opposite direction indicated by arrow 206.

Figure 3:
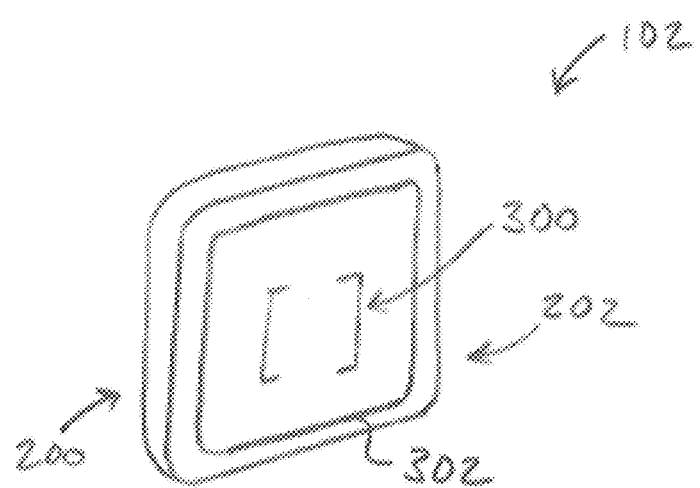
FIG. 3 is a back view of one embodiment of the medical device.

A back view of one embodiment of the medical device 100 is shown in FIG. 3. In some embodiments, the medical device 100 can include an aiming feature 300. The aiming feature 300 can be any feature that can be used to achieve a desired relative orientation of the medical device. In some embodiments, the aiming feature 300 can comprise a reticle, a visible laser designator, open sights, aperture sights, or the like.

In some embodiments, and as depicted in FIG. 3, the aiming feature 300 can be located within and/or be a part of a screen or display 302. In some embodiments, the display 302 can show all or portions of image data generated by the image data generator 208. In some embodiments, for example, the display 302 can show live video of image data captured and/or generated by the image data generator 208.

This video, combined with the aiming feature 300 can be used to align the device 102 so that the pairing module 203 of one device 102 is pointed at the pairing module 203 of another device 102. More specifically, the aiming feature 300 can be used to align the device 102 so that the image data generator 208 of the device 102 is pointed in a desired direction, and specifically so that the image data generator 208 of the device 102 is pointed at another device 102. In some embodiments, this video, combined with the aiming feature 300 can be used to align the device 102 so that the image data generator 208 of the device 102 is pointed at the visual output 204 of another device 102. In some embodiments, this can include the pointing of the image data generator 208 of the second device 102-B at the visual output 204 of the first device 102-A as shown in FIG. 1. In such a configuration, the first device 102-A can transmit data via modulation of the pairing module 203 and more specifically of the visual output 204, which modulation of the pairing module 203 and more specifically of the visual output 204 can be captured by the second device 102-B in the form of image data generated by the pairing module 203 of the second device 102-B and more specifically in the form of image data generated by the image data generator 208. This image data can be analyzed to extract the data transmitted from the first device 102-A, which data can be used to securely couple the first and second devices 102-A, 102-B. In some embodiments, after the coupling of the first and second devices 102-A, 102-B, further data can be exchanged between the devices via radio wave transmissions, via manipulation of the visual output 204, or via a combination of radio wave transmissions and manipulation of the visual output 204. In some embodiments, the visual output 204 can be controlled and/or manipulated to generate a visual indicator, also referred to herein as a visual identifier.

Figure 4:
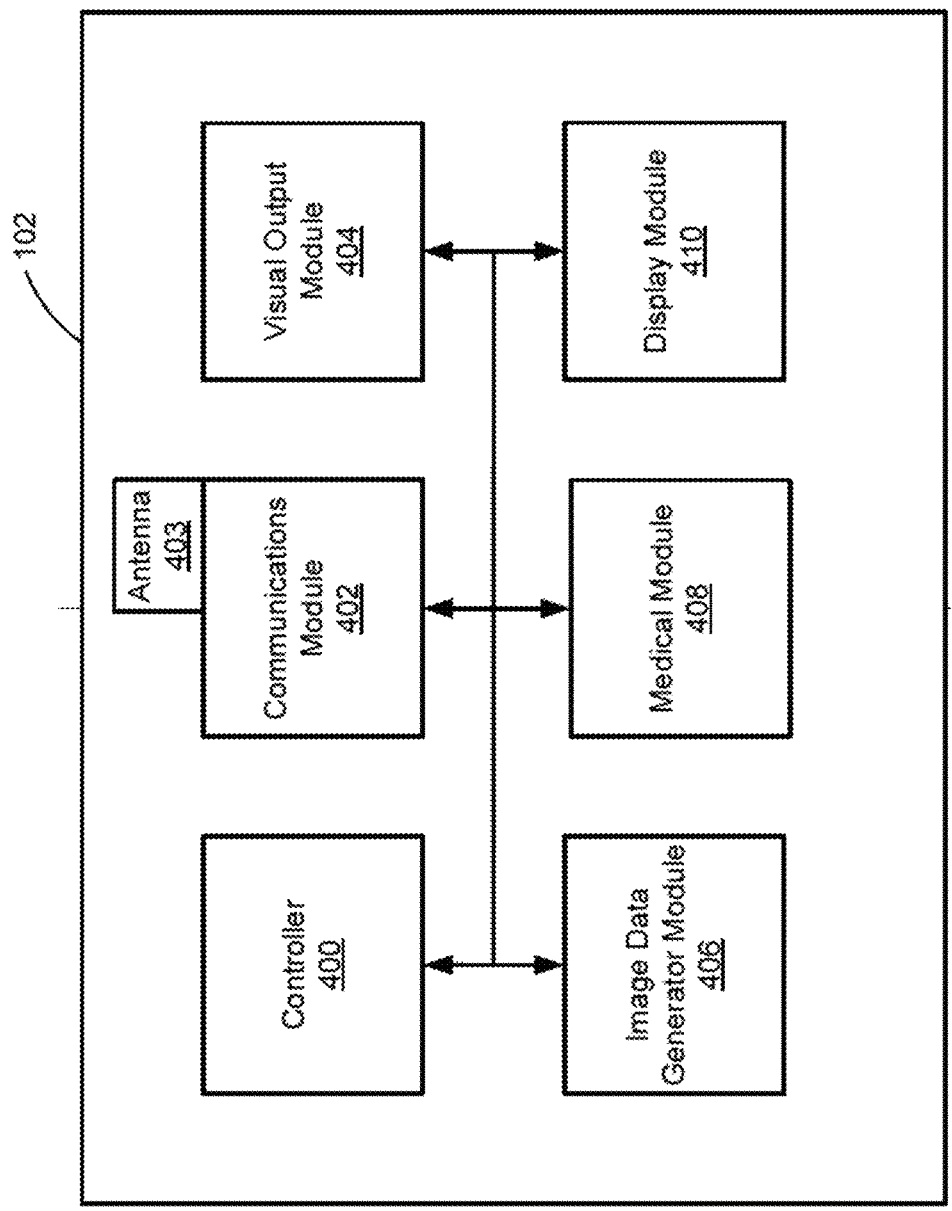
FIG. 4 is a schematic illustration of modules of one embodiment of the medical device.

FIG. 4 is a schematic illustration of modules of one embodiment of the device 102. The device 102 can include controller 400 which can direct operation of other modules of the device 102 including sending information to other modules of the device 102 and receiving information from other modules of the device 102.

The controller 400 can comprise, for example, one or several processors and a memory. In some embodiments, the processor can provide instructions to and receive information from the other modules of the device 102 and/or from other medical devices 102 in the medical device network 100. The processor can act according to stored instructions, which stored instructions can be located in the memory. The memory can be associated with the processor. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

The device 102 can include a communications module 402 that can include, for example, an antenna 403. The communications module 402 can include a transceiver or similar hardware to allow the communications module 402 to send data to other medical devices 102 in the medical device network 100 and to receive data from other medical devices 102 in the medical device network 100. In some embodiments, the communications module 402 can send data and receive data via radio wave-based communications via the antenna, and in some embodiments, the communications module 402 can control and/or interact with one or both of a visual output module 404 and an image data generator module 406 to send and/or receive data from another device 102 in the medical device network 100. In some embodiments, the visual output module 404 and the image data generator module 406 can be combined into a single pairing module.

The visual output module 404 can comprise a hardware or software module and can include the visual output 204. In some embodiments, the visual output module 404 can be configured to control the generation of a visual indicator by the visual output 204 according to instructions received from, for example, the controller 400 and/or the communications module 402. The visual output module 404 can control one or several attributes of the visual indicator including, for example, a frequency of EMR emitted by visual output 204, an intensity of EMR emitted by the visual output 204, a duration of generation of EMR by the visual output 204, a pattern of EMR generated by the visual output 204, or the like. In some embodiments, for example, by controlling one or several attributes of the visual indicator by control of the visual output 204, the visual output module 404 can embed and/or encode data within the visual indicator.

The image data generator module 406 can interact with the image data generator 208 to generate image data. The image data generator module 406 can comprise a hardware or software module. This can include, for example, controlling the image data generator 208 to start generating image data and/or to stop generating image data. In some embodiments, the image data generator module 406 can control the image data generator 208 according to instructions received from, for example, the controller 400 and/or the communications module 402. In some embodiments, the image data generator module 406 can evaluate generated image data to extract any embedded and/or encoded information from the image data.

The device 102 can include a medical module 408. The medical module 408 can comprise a hardware or software module, and can control the performing of a medical function, such as, for example, pumping blood, by the device 102. In some embodiments, the medical module 408 of one device 102 can act, in part, according to instructions and/or data received from another medical device. In one embodiment, for example, the first device 102-A can comprise an implantable device and the second device 102-B can comprise an external controller. In such an embodiment, the first device 102-A can operate according to controls and/or parameters received from the second medical device. In some embodiments, the first device 102-A can comprise an active implantable device and the second device 102-B can comprise a sensor. In such an embodiment, the second device 102-B can provide sensed data to the first device 102-A and the first device 102-A can operate, in part, according to the sensed data.

The device 102 can include a display module 410. The display module 410 can comprise a hardware or software module. The display module 410 can comprise the display 302. In some embodiments, the display module 410 can control the display 302 to display image data generated by the image data generator module 406.

Figure 5:
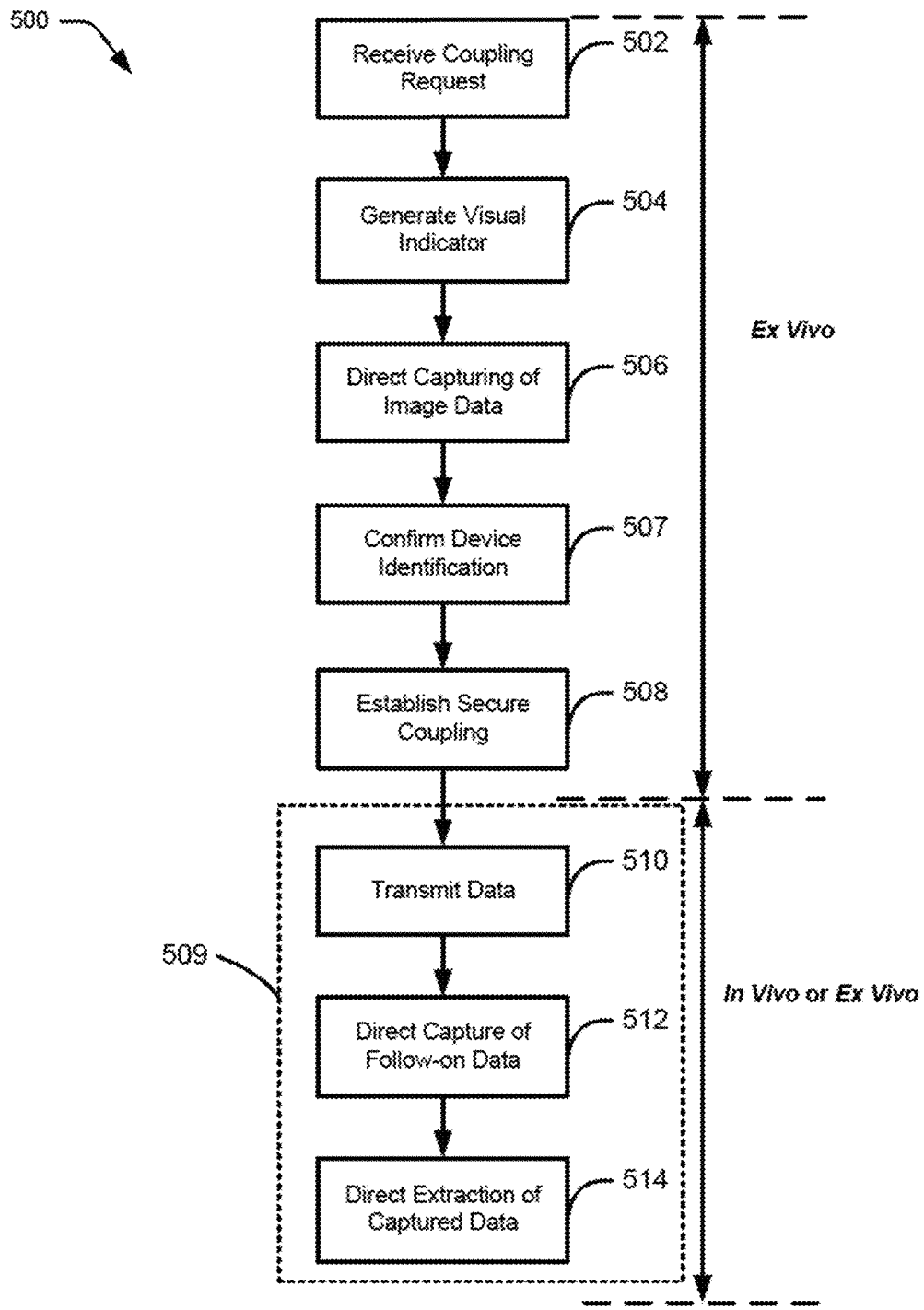
FIG. 5 is a flowchart illustrating one embodiment of a process for securely coupling medical devices.

FIG. 5 is a flowchart illustrating one embodiment of a process 500 for securely coupling medical devices 102 and/or for securely transmitting data between medical devices 102. The process 500 can be performed by all or portions of the medical device network 100 including, for example, by one or more of the medical devices 102. In some embodiments, the process 500 can include a first portion that can be, for example, performed ex vivo, and the second portion that can be, for example, be performed either in vivo or ex vivo.

The process 500 begins a block 502 wherein a coupling request is received. The coupling request can be received by a device 102 such as, for example, by the first device 102-A from a user or from another device and/or component of the medical device network 100. After the receipt of the coupling request, the process 500 proceeds to block 504, wherein the visual identifier is generated. In some embodiments, this can include the generation of one or several control signals by the controller 400 and/or the communications module 404. These one or several control signals can direct the generation and/or the generating of the visual indicator by the visual output 204 of the first device 102-A. In some embodiments, for example, the visual indicator can encode data from the first device 102-A for receipt by the second device 102-B. In some embodiments, this data can be encoded in modulation of the visual indicator or in pulses of the visual indicator such as, for example, the controlled blinking of the visual indicator. In some embodiments, this modulation can comprise modulating and intensity of the visual output 204 of the first device 102-A such as by, for example, the blinking of the visual output 204 or the selectively dimming of the visual output 204.

In some embodiments, this blinking can be according to a specific and/or predetermined timing to allow syncing of first and medical devices 102-A, 102-B. In some embodiments, this blinking can encode a passcode or security key such as a passcode of, for example, 16 or fewer bits, and in some embodiments, this blinking can encode a complete public encryption key. This public encryption key can be used to access a wireless communication system and/or wireless communication network such as, for example, the medical device network 100. In some embodiments, the complete encryption key can comprise at least 128 bits of data.

After the visual indicator has been generated, the process 500 proceeds to block 506, wherein image data is captured. In some embodiments, the step of block 506 can comprise the directing, by the first device 102-A, of the capturing of image data by the second device 102-B. In some embodiments, for example, the first device 102-A can direct the second device 102-B to capture image data of a device 102 that can be an, at least at that instant, unidentified device 102. In some embodiments, this direction to capture image data can be sent in the form of one or several radio waves by the communications module 402 of the first device 102-A via the antenna 403 and can be decoded and/or unencrypted such that the second device 102-B can receive the direction without a pre-existing secure connection between the first and second devices 102-A, 102-B.

In response to receipt by the second device 102-B of the direction to capture image data, the second device 102-B can activate the image data generator 208 with the image data generator module 406 and can capture image data which can comprise a series of time-sequential images, and/or video data. In some embodiments, this can include the providing of instructions for a user to point the image data generator 208 of the second device 102-B towards the as yet unidentified device 102. This can further include the activation of the display 302 to display image data to allow the aiming of the second device 102-B. The image data and/or video data can be captured with a frame rate and/or frequency sufficient to capture and/or resolve the pulsation and/or blinking of the visual output 208. In some embodiments, the image data and/or video data can be captured at a frame rate and/or at a frequency that is at least as high as a highest frequency of pulsation and/or blinking of the visual output 208, at least twice as fast as the highest frequency of pulsation and/or blinking of the visual output 208, at least five times as fast as the highest frequency of pulsation and/or blinking of the visual output 208, at least 10 times as fast as the highest frequency of pulsation and/or blinking of the visual output 208, at least 20 times as fast as the highest frequency of pulsation and/or blinking of the visual output 208, and/or any other or intermediate frame rate and/or frequency. In some embodiments, this frequency and/or frame rate can be specified or indicated in the direction to begin capturing image data from the first device 102-A.

After the directing of the capturing of image data and/or after the capturing of the image data, the process 500 proceeds to block 507 wherein device identification is confirmed. This can include confirming that the previously unidentified device 102, at which the image data generator 208 of the second device 102-B is pointed, is the first device 102-A. In some embodiments, determining that the previously unidentified device 102 is the first device 102-A can include an evaluation of the generated image data. This evaluation of the generated image data can include a determination of whether the image of the unidentified device 102 matches the image of the first device 102-A, or specifically, whether a shape of the unidentified device 102 matches a shape of the first device 102-A.

In some embodiments, the evaluation of the generated image data can include identifying the visual identifier within the image data. The identifying of the visual identifier within the image data can include, for example, identifying the modulation of the visual output 204 of the first device 102-A. The identifying of the visual identifier within the image data can further include extracting data from the identified modulation of the visual output 204 of the first device 102-A. This extracted data can be, for example, transmitted to the first device 102-A from the second device 102-B in the form of one or several radio waves via, for example, the antennas 403 of the first and second devices 102-A, 102-B.

The extracted data can, in some embodiments, be compared to data indicating one or several attributes of the visual identifier. In some embodiments, this can include comparing the modulation of visual output 204 as captured in the image data to the actual modulation of the visual output 204 of the first device 102-A. If it is determined that the extracted data from the second device 102-B matches the data indicating one or several attributes of the visual identifier, then the unidentified device 102 can be confirmed as the first device 102-A.

After the device identification has been confirmed, the process 500 proceeds to block 508 wherein a secure coupling is established. In some embodiments, this secure coupling can be established between the first device 102-A and the second device 102-B. In some embodiments, the secure coupling can be established when the unidentified device 102 is identified as the first device 102-A. In some embodiments, this secure coupling can be established based on the security key embedded in the modulation of the visual output 204. In some embodiments, the steps of blocks 502 through 508 can be performed ex vivo.

After the establishment of a secure coupling between the first device 102-A and the second device 102-B, the process 500 proceeds to block 509 wherein information is transmitted and/or communicated subsequent to the establishment of secure coupling between the medical devices 102 and specifically subsequent to the establishment of secure coupling between the first device 102-A and the second device 102-B. In some embodiments, the step of block 509 can be performed in vivo or ex vivo. In embodiments in which the step of block 509 is performed in vivo, one or both of the first and second devices 102-A, 102-B can be implanted within the body of the patient to create an at least partial in vivo state of one or both of the first and second devices 102-A, 102-B.

In some embodiments, the communication and/or transmission of data subsequent to the establishment of secure coupling between the medical devices 102 can be divided into multiple steps, and specifically into the steps indicated in block 510 through 514. At block 510 data is communicated and/or transmitted between the first device 102-A and the second device 102-B. Data which is communicated and/or transmitted subsequent to the establishing of a secure coupling and/or secure communication connection between the medical devices 102, and specifically between the first device 102-A and the second device 102-B, is referred to herein as follow-on data. The communicating and/or transmitting data between the medical devices 102 can include transmitting and/or communicating information from the first device 102-A to the second device 102-B, and/or transmitting and/or communicating information from the second device 102-B to the first device 102-A. In some embodiments, this data can be communicated and/or transmitted via further modulation of the visual output 204 and/or, in some embodiments, this data can be communicated and/or transmitted via one or several radio waves. In some embodiments, for example, information can be communicated and/or transmitted from the first device 102-A to the second device 102-B via radio wave and/or modulation of the visual output 204, and/or information can be communicated and/or transmitted from the second device 102-B to the first device 102-A via radio wave and/or modulation of the visual output 204. In embodiments in which step 510 is performed in vivo, information, may be transmitted and/or communicated via radio wave as sightlines may be obstructed via tissue, and thus communication via modulation of the visual output 204 may be ineffective. In some embodiments, due to proximity between the medical devices 102, and/or the frequency of EMR generated by the visual output 204, in vivo communication via modulation of the visual output 204 may be effective.

At block 512, the data transmitted in block 510 can be received and/or captured. In some embodiments in which the transmitted data is transmitted via radio wave, the communication can be received via the antenna 403 of the receiving medical device, which receiving medical device can be one of the first device 102-A and the second device 102-B. In embodiments in which the transmitted data is transmitted via modulation of the visual output 204, the communication can be received and/or captured via the image data generator 208 and the generation of image data by the image data generator 208. As discussed above, the image data can comprise a series of time-sequential images, and/or video data. In some embodiments, the images, or video data can be captured with a frequency and/or have a frame rate sufficient to capture and/or resolve the pulsation and/or blinking of the visual output 208.

At block 514, captured data can be extracted. In some embodiments, this can include evaluation of image data to determine the modulation of the visual output 204, and/or evaluation of electrical signals generated in response to receipt of radio waves by the antenna 403. In some embodiments, the communication of step 509 can continue until all desired information has been communicated and/or transmitted between the medical devices 102.

Figure 6:
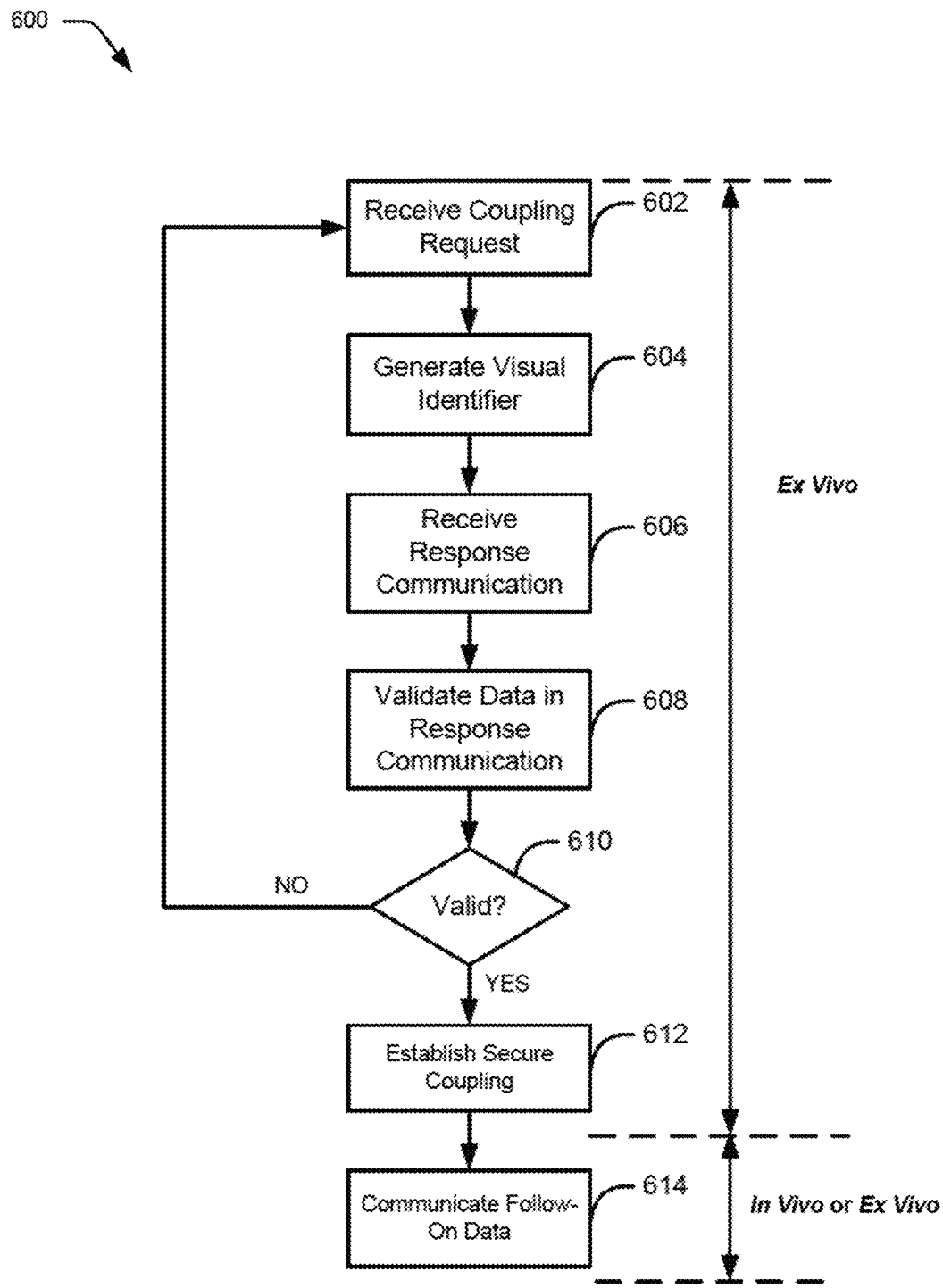
FIG. 6 is a flowchart illustrating one embodiment of a process for modulating a visual output to securely couple medical devices.

FIG. 6 is a flowchart illustrating one embodiment of a process 600 for modulating a visual output to securely couple medical devices 102 and/or to securely transmit data between medical devices 102. The process 600 can be performed by, for example, the first device 102-A. In some embodiments, the process 600 can include a first portion that can be, for example, performed ex vivo, and the second portion that can be, for example, be performed either in vivo or ex vivo. In some embodiments, for example, the steps indicated by blocks 602 through 612 can be performed ex vivo and the steps indicated by block 614 can be performed in vivo, ex vivo, or a combination of in vivo and ex vivo.

The process 600 begins a block 602 wherein a coupling request is received. The coupling request can be received by the first device 102-A from a user or from another device, or component of the medical device network 100. After the receipt of the coupling request, the process 600 proceeds to block 604, wherein the visual identifier is generated. In some embodiments, this can include the generation of one or several control signals by the controller 400 and/or the communications module 404 to control the operation of the visual output 204 to generate the visual identifier and/or to create a modulated or patterned visual indicator.

After the generating of the visual identifier, the process 600 proceeds to block 606 wherein a response communication is received. In some embodiments, the response communication can be received from a second device 102-B. This response communication can be received in the form of a modulated visual identifier captured by the image data generator 208 of the first device 102-A, and in some embodiments, this response communication can be received in the form of one or several radio wave transmissions received by the antenna 403 of the first device 102-A.

After the response communication has been received, the process 600 proceeds to block 608, wherein data received in the response communication is validated. In some embodiments, this can include extracting data from the response communication, which data can, for example, be data extracted from image data generated by the second device 102-B. The data extracted from the received response data can then be compared to data used to control the visual output 204 to generate the visual identifier and/or to generate the modulations and/or pulsation of the visual identifier. If it is determined, as indicated at decision step 610, that the received response communication is invalid, then the process 600 can return to block 602 and proceed as outlined above. If it is determined that the received response communication is valid, then the process 600 can proceed to block 612. In some embodiments, the determination of validity of the received response communication is based on the comparison of the received response communication and data used to generate the visual identifier. If there is a match between the received response indication and/or data included in the received response communication and the data used to generate the visual identifier, then the response indication and/or the request coupling with the source device of the response indication can be validated.

At block 612, secure coupling between the first device 102-A and the second device 102-B is established. In some embodiments, this secure coupling can be established based on data encoded in the visual identifier generated in block 604, which data can be returned to the first device 102-A from the second device 102-B via the response communication. This data encoded in the visual identifier generated in block 604 can serve as a key and/or token to maintain and/or perpetuate the secure coupling between the first device 102-A and the second device 102-B.

At block 614, any follow-on data is communicated. In some embodiments, this follow-on data can be communicated subsequent to the establishment of a secure coupling, and the following data can be communicated via radio wave, via modulation of the visual output 204 and generation of image data, or via a combination of radio wave and modulation of the visual output 204 and generation of image data. In some embodiments, this communication can be enabled and/or allowed via the established secure coupling, and in some embodiments, data encoded in the visual identifier generated in block 604 can be used as a key or token to enable the communication of follow-on data.

Figure 7:
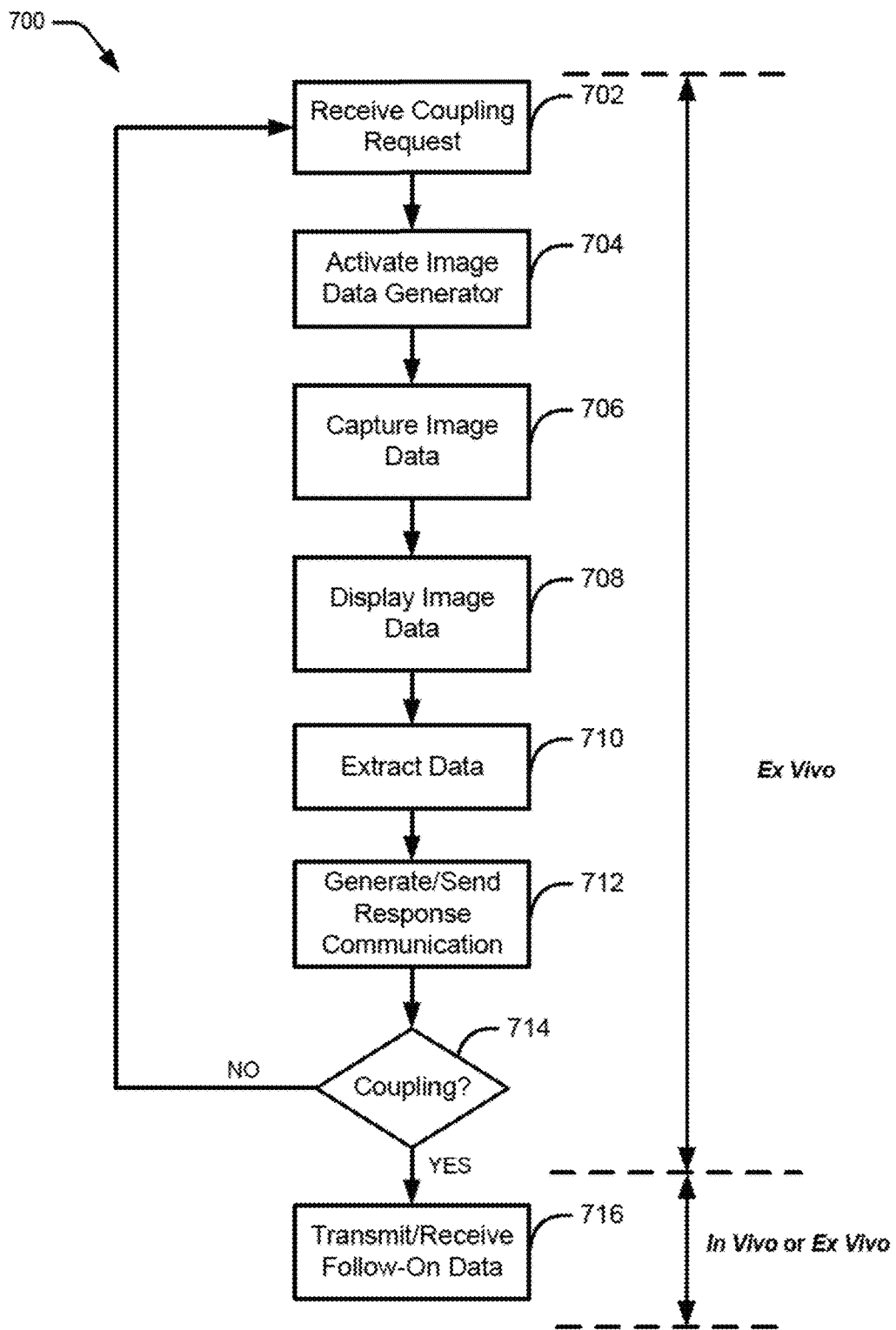
FIG. 7 is a flowchart illustrating one embodiment of a process for capturing and analyzing image data to securely couple medical devices.

FIG. 7 is a flowchart illustrating one embodiment of a process 700 for capturing and analyzing image data to securely couple medical devices 102 and/or to securely transmit data between medical devices 102. The process 700 can be performed by, for example, the second device 102-B. In some embodiments, the process 700 can include a first portion that can be, for example, performed ex vivo, and the second portion that can be, for example, be performed either in vivo or ex vivo. In some embodiments, for example, the steps indicated by blocks 702 through 714 can be performed ex vivo and the steps indicated by block 716 can be performed in vivo, ex vivo, or a combination of in vivo and ex vivo.

The process 700 begins a block 702 wherein a coupling request is received. The coupling request can be received by the second device 102-B from a user, from the first device 102-A, or from another device, or component of the medical device network 100. After the receipt of the coupling request, the process 700 proceeds to block 704, wherein the image data generator 208 of the second device 102-B is activated. In some embodiments, the image data generator 208 can be activated in response to the received coupling request and the activation of the image data generator 208 can be based on one or several control signals generated by the controller 400 and provided to the image data generator module 406.

After the image data generator has been activated, the process 700 proceeds to block 706, wherein image data is captured and/or generated. This image data can be captured or generated in response to receipt of direction from the first device 102-A to capture and/or generate image data. In some embodiments, the image data can be captured and/or generated by the image data generator 208. In some embodiments, the controller 400 of the second device 102-B can generate and send one or several control signals to the image data generator module 406, directing the capture of image data. In some embodiments, this image data can be captured for a predetermined amount of time and/or can be captured until a stop signal is received from the controller 400. In some embodiments, the image data can comprise a series of time sequential images and/or video data.

After or simultaneous with the capture of image data, image data is displayed and/or can be displayed as indicated by block 708. In some embodiments, the image data can be displayed by the displays 302 of the second device 102-B. The display of the image data can facilitate in aiming the image data generator 208 of the second device 102-B at the first device 102-A and specifically at the visual output 204 of the first device 102-A.

After the capture of image data, the image data can be analyzed and data can be extracted from the image data. In some embodiments, this data can be encoded into the visual identifier, and specifically encoded into the pulsation or modulation of the visual identifier. In some embodiments, the extracting of this data from the image data can include the identification of pulsations or modifications in the image data, and specifically in the time sequential series of images in the image data in the decoding of those pulsations or modifications.

After the data has been extracted, the process 700 proceeds to block 712 wherein a response communication is generated and sent. In some embodiments, the response communication can comprise the data extracted from the image data, the image data, an evaluation of the data extracted from the image data, or the like. The response communication can be generated and sent via the communications module 402 and the antenna in the form of radio waves, or via the communications module 402, the visual output module 404, and the visual output 208. In the form of a visual identifier.

After the sending of the response communication, the process 700 can proceed to decision step 714 wherein it is determined whether a secure coupling has been established. In some embodiments, this can include determining whether confirmation of a match between data extracted from the image data and data used to generate the visual identifier by the first device 102-A is received. If it is determined that secure coupling has not been established, then the process 700 returns to block 702 and proceeds as outlined above. Alternatively, in some embodiments, if a secure coupling has not been established, the second device 102-B can establish a secure communication connection with the first medical device based on the data extracted from the visual identifier as captured in the image data.

If it is determined that secure coupling has been established, the process 700 proceeds to block 716, wherein any follow-on data is communicated. In some embodiments, this follow-on data can be communicated, subsequent to the establishment of a secure coupling and the following data can be communicated, via radio wave, via modulation of the visual output 204 and generation of image data, or via a combination of radio wave and modulation of the visual output 204 and generation of image data. In some embodiments, this communication can be enabled and/or allowed via the established secure coupling, and in some embodiments, data encoded in the visual identifier generated in block 604 can be used as a key or token to enable the communication of follow-on data.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context and may all methods described herein are not limited to the steps or order of steps disclosed herein. For example, these methods disclosed herein may be performed with additional steps, and/or as parts of other processes. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention, similarly, non-claimed method step should be construed as essential.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of bi-modal communication between medical devices, the method comprising:
   generating with a first medical device a visual identifier of the first medical device, wherein generating the visual identifier comprises modulating a light source of the first medical device;
   directing capture of image data of an unidentified medical device with a second medical device;
   determining that the unidentified medical device is the first medical device based on the captured image data, wherein the determining comprises comparing the image data of the unidentified medical device to the modulation of the light source of the first medical device; and
   establishing a secure communication connection between the first and second medical devices.

2. The method of claim 1, wherein the image data comprises a series of time-sequential images.

3. The method of claim 1, wherein the image data comprises video data.

4. The method of claim 1, wherein determining that the unidentified medical device is the first medical device comprises identifying the visual identifier within the image data.

5. The method of claim 1, wherein the modulation of the light source of the first medical device comprises modulating at least one of: an intensity of the light source of the first medical device; a frequency of the light source; or a frequency of light emitted by the light source.

6. The method of claim 4, wherein identifying the visual identifier within the image data comprises identifying the modulation of the light source of the first medical device and extracting data from the identified modulation of the light source of the first medical device.

7. The method of claim 4, wherein determining that the unidentified medical device is the first medical device comprises identifying a shape of the first medical device within the image data.

8. The method of claim 1, further comprising transmitting data from the first medical device to the second medical device via modulation of a light emitter subsequent to establishing a secure communication connection between the first and second medical devices.

9. The method of claim 8, further comprising:
   capturing follow-on image data of the modulation of the light emitter subsequent to establishing the secure communication connection between the first and second medical devices; and
   extracting transmitted data from the follow-on image data.

10. The method of claim 1, further comprising transmitting data from the second medical device to the first medical device.

11. The method of claim 10, wherein data is transmitted from the second medical device to the first medical device via a wireless communication.

12. The method of claim 11, wherein the data is transmitted from the second medical device to the first medical device in response to the captured image data.

13. A system comprising:
    a first medical device comprising:
      an antenna;
      a visual output; and
      a processor, wherein the processor is configured to generate a first visual identifier comprising data identifying the first medical device with the visual output, wherein generating the visual identifier comprises directing modulation of a light source of the first medical device; and
    a second medical device comprising:
      an antenna;
      a camera configured to capture image data; and
      a processor configured to:
        identify the visual identifier within the captured image data;
        extract data from the visual identifier as captured in the image data;
        determine that the visual identifier is associated with the first medical device, wherein the determination comprises comparing the extracted data to the modulation of the light source of the first medical device; and
        establish a secure communication connection with the first medical device based on the data extracted from the visual identifier as captured in the image data.

14. The system of claim 13, wherein the captured image data comprises a series of time-sequential images.

15. The system of claim 13, wherein identifying the visual identifier within the image data comprises identifying the modulation of the light source of the first medical device and extracting data from the identified modulation of the light source of the first medical device.

16. The system of claim 13, wherein the processor of the first medical device is further configured to transmit data from the first medical device to the second medical device via modulation of a light emitter subsequent to establishing a secure communication connection between the first and second medical devices.

17. The system of claim 16, wherein the camera is configured to capture follow-on image data of the modulation of the light emitter subsequent to establishing the secure communication connection between the first and second medical devices; and wherein the processor of the second medical device is configured to extract transmitted data from the follow-on image data.

18. The system of claim 13, wherein the second medical device comprises an antenna, and wherein the first and second medical devices are configured to wirelessly communicate via the antenna of the first medical device and the antenna of the second medical device.

19. The system of claim 13, wherein the captured image data comprises video data.

20. The system of claim 13, wherein the modulation of the light source of the first medical device comprises modulation of at least one of: an intensity of the light source of the first medical device; a frequency of the light source; or a frequency of light emitted by the light source.

21. The system of claim 13, wherein a processor is further configured to identify a shape of the first medical device within the captured image data.

* * * * *